(12) United States Patent
Hölzemann et al.

(10) Patent No.: US 7,432,282 B2
(45) Date of Patent: Oct. 7, 2008

(54) PYRIDINALKYL-AMINOALKYL-IH-INDOLE DERIVATIVES HAVING AN INHIBITORY ACTION ON 5-HT AND SEROTONIN REUPTAKE AS ANTIDEPRESSANTS AND ANXIOLYTICS

(75) Inventors: Günter Hölzemann, Seeheim-Jugenheim (DE); Kai Schiemann, Darmstadt (DE); Timo Heinrich, Groβ-Umstadt (DE); Henning Böttcher, Darmstadt (DE); Joachim Leibrock, Pfungstadt (DE); Christoph van Amsterdam, Darmstadt (DE); Gerd Bartoszyk, Weiterstadt (DE); Christoph Seyfried, Seeheim-Jugenheim (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 326 days.

(21) Appl. No.: 10/535,916

(22) PCT Filed: Oct. 30, 2003

(86) PCT No.: PCT/EP03/12081

§ 371 (c)(1),
(2), (4) Date: May 23, 2005

(87) PCT Pub. No.: WO2004/047840

PCT Pub. Date: Jun. 10, 2004

(65) Prior Publication Data

US 2006/0063811 A1   Mar. 23, 2006

(30) Foreign Application Priority Data

Nov. 22, 2002  (DE) ................ 102 54 596

(51) Int. Cl.
*A61K 31/4709* (2006.01)
*A61K 31/4439* (2006.01)
*C07D 215/12* (2006.01)
*C07D 401/12* (2006.01)

(52) U.S. Cl. .......................... 514/314; 514/337; 546/164; 546/176; 546/277.4

(58) Field of Classification Search ............. None
See application file for complete search history.

(56) References Cited

U.S. PATENT DOCUMENTS

| 5,998,630 | A | 12/1999 | Fritz et al. |
| 6,126,932 | A | 10/2000 | Fritz et al. |
| 2004/0019044 | A1 | 1/2004 | Dorsch et al. |

FOREIGN PATENT DOCUMENTS

| WO | WO 9620191 | 7/1996 |
| WO | WO 97 13512 | 4/1997 |
| WO | WO 0198293 | 12/2001 |

OTHER PUBLICATIONS

Ho, et al. "Synthesis of 1-aryl(and 1-aralkyl)-β-carbolines", Canadian Journal of Chemistry, vol. 45, pp. 2963-2967. (1967).*
Xiong, et al. Am J. Cadiol. 98(1), pp. 42-47, 2006.*
J. Med. 354(20), pp. 2188-2190, 2006.*
Vacher, Bernard et al.: "Design and Synthesis of a series of 6-Substituted 2-Pyridinylmethylamine Derivatives as Novel, High-Affinity, Selective Agonists at 5 - HT1A Receptors" Journal of Medicinal Chemistry (1998), Seite 1, verbindung 77, Seite 5075.
Yajima, Tatsuo et al.: "Conformational Preference of the Side Chain Aromatic Ring in Cu(II) and Pd(II) Complexes of 2N10-Donor Ligands" Inorganica Chimica Acta (2002), seite 195.

* cited by examiner

Primary Examiner—Rebecca L Anderson
Assistant Examiner—Michael P Barker
(74) Attorney, Agent, or Firm—Millen, White, Zelano & Branigan, P.C.

(57) ABSTRACT

Novel indole derivatives of the formula (I), in which X, Y, $R^1$, $R^{1'}$, m and n have the meanings indicated in Patent Claim 1, have a strong affinity to the $5$-$HT_{1A}$ and in some cases to the $5$-$HT_{1D}$ receptors. The compounds inhibit serotonin reuptake, exhibit serotonin-agonistic and -antagonistic properties and are suitable as antidepressants, anxiolytics and for the treatment of neurodegenerative diseases (I)

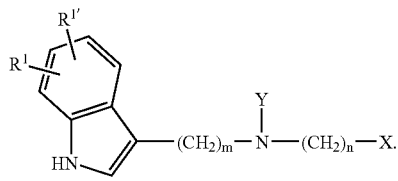

11 Claims, No Drawings

PYRIDINALKYL-AMINOALKYL-IH-INDOLE DERIVATIVES HAVING AN INHIBITORY ACTION ON 5-HT AND SEROTONIN REUPTAKE AS ANTIDEPRESSANTS AND ANXIOLYTICS

The invention relates to indole derivatives of the formula I

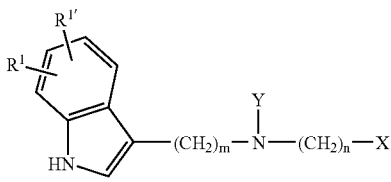

in which

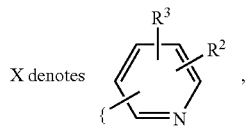

Y denotes H or A', $R^1$, $R^{1'}$ each, independently of one another, denote H, A, OH, OA, CN, Hal, $COR^4$ or $CH_2R^4$, $R^2$ denotes H, A, Hal, OH, OA, SA, COOH, COOA', CHO, COA', $SO_2A'$, $NH_2$, NHA, $NA_2$, $CH_2NA_2$, NHCOA, NHCOAr, NHCOOA, $NHSO_2A$, $NHSO_2Ar$, $CH_2NHSO_2A$, $NHCONH_2$, NHCONHA, $NHCONA_2$, NHCONHAr, $CONH_2$, CONHA, $CONA_2$, $SO_2NH_2$, $SO_2NHA$, $SO_2NA_2$, $CH_2SO_2NH_2$, $CH_2SO_2NHA$, $CH_2SO_2NA_2$, $[C(R^4R^{4'})]_pCN$, $[C(R^4R^{4'})]_pCF_3$, $[C(R^4R^{4'})]_pCOR^4$, $[C(R^4R^{4'})]_pAr$, $—O—[C(R^4R^{4'})]_pAr$ or $[C(R^4R^{4'})]_pHet$, $R^3$ denotes H, A, $[C(R^4R^{4'})]_pAr$ or $[C(R^4R^{4'})]_pHet$, $R^2$ and $R^3$ together also denote —CH=CH—CH=CH—, —CH=CH—CH$_2$—C—H$_2$— or —CH$_2$—CH$_2$—CH=CH—, in which 1 or 2 CH and/or CH$_2$ units may be replaced by N and/or 1, 2, 3 or 4 H atoms may be substituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$ or $S(O)_oA$, —O—CH$_2$—O— or —O—CH$_2$—CH$_2$—O—, $R^4$, $R^{4'}$ each, independently of one another, denote H, A, OH, OA, $NH_2$, NHA, $NA_2$ or NHCOOA', Ar denotes phenyl, naphthyl or biphenyl, each of which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$ or $S(O)_oA$, Het denotes a mono- or bicyclic saturated, unsaturated or aromatic heterocycle having 1 to 4 N, O and/or S atoms, which may be unsubstituted or mono-, di- or trisubstituted by carbonyl oxygen, =S, =NH, Hal, A, —(CH$_2$)$_o$—Ar, —(CH$_2$)$_o$-cycloalkyl, —(CH$_2$)$_o$—OH, —(CH$_2$)$_o$—NH$_2$, $NO_2$, CN, —(CH$_2$)$_o$—COOH, —(CH$_2$)$_o$—COOA, —(CH$_2$)$_o$—CONH$_2$, —(CH$_2$)$_o$—NHCOA, $NHCONH_2$, —(CH$_2$)$_o$—NHSO$_2$A, CHO, COA', $SO_2NH_2$ and/or $S(O)_oA$, A denotes unbranched or branched alkyl having 1-10 C atoms, in which one or two CH$_2$ groups may be replaced by —CH=CH— groups and/or 1-7 H atoms may also be replaced by F and/or Cl, A' denotes alkyl having 1 to 6 C atoms or benzyl, Hal denotes F, Cl, Br or I and m denotes 2, 3, 4, 5 or 6 n denotes 1, 2, 3 or 4, o denotes 0, 1 or 2, p denotes 0, 1, 2, 3, 4, 5 or 6, and pharmaceutically usable derivatives, solvates and stereoisomers thereof, including mixtures thereof in all ratios.

The invention had the object of finding novel compounds having valuable properties, in particular those which are used for the preparation of medicaments.

Heterocyclic aminoalkylpyridine derivatives are described in WO 01/98293. The present invention is to be regarded as a selection invention hereto.

Other indole derivatives are known from WO 94/24127, WO 90/05721 or from JP 05043544.

It has been found that the compounds of the formula I according to the invention and physiologically acceptable acid-addition salts thereof are well tolerated and have valuable pharmacological properties since they have actions on the central nervous system, in particular 5-HT reuptake-inhibiting actions, in that they influence serotoninergic transmission. In particular, they have a strong affinity to the 5-HT$_{1A}$ and in some cases to the 5-HT$_{1D}$ receptors.

Since the compounds also inhibit serotonin reuptake, they are particularly suitable as antidepressants and anxiolytics. The compounds exhibit serotonin-agonistic and -antagonistic properties. They inhibit the binding of tritiated serotonin ligands to hippocampal receptors (Cossery et al., European J. Pharmacol. 140 (1987), 143-155) and inhibit synaptosomal serotonin reuptake (Sherman et al., Life Sci. 23 (1978), 1863-1870). Ex-vivo demonstration of serotonin reuptake inhibition is carried out using synaptosomal uptake inhibition (Wong et al., Neuropsychopharmacol. 8 (1993), 23-33) and p-chloroamphetamine antagonism (Fuller et al., J. Pharmacol. Exp. Ther. 212 (1980), 115-119). The 5-HT$_{1D}$ affinity can be determined, for example, by the method described by Pauwels and Palmier in Neuropharmacology, 33, 67 (1994).

The binding properties of the compounds of the formula I can be determined by known 5-HT$_{1A}$ (serotonin) binding tests (5-HT$_{1A}$ (serotonin) binding test: Matzen et al., J. Med. Chem., 43, 1149-1157, (2000) in particular page 1156 with reference to Eur. J. Pharmacol.: 140, 143-155 (1987).

The compounds according to the invention can be employed for the treatment of diseases which are associated with the serotonin neurotransmitter system and in which high-affinity serotonin receptors (5-HT$_{1A}$ receptors) and/or 5-HT$_{1D}$ receptors are involved.

The compounds of the formula I are therefore suitable both in veterinary and also in human medicine for the treatment of dysfunctions of the central nervous system and of inflammation. They can be used for the prophylaxis and combating of the consequences of cerebral infarction (apoplexia cerebri), such as strokes and cerebral ischaemia, and for the treatment of extrapyramidal motor side effects of neuroleptics and of Parkinson's disease, for acute and symptomatic therapy of Alzheimer's disease and for the treatment of amyotrophic lateral sclerosis. They are likewise suitable as therapeutic agents for the treatment of brain and spinal cord trauma. In particular, however, they are suitable as medicament active ingredients for anxiolytics, antidepressants, antipsychotics, neuroleptics, antihypertonics and/or for positively influencing obsessive-compulsive disorder (OCD), anxiety states, panic attacks, psychoses, anorexia, delusional obsessions, migraine, Alzheimer's disease, sleeping disorders, tardive dyskinesia, learning disorders, age-dependent memory impairment, eating disorders, such as bulimia, drugs misuse and/or sexual dysfunctions.

An important indication for the administration of the compound of the general formula I are psychoses of all types, in particular mental illnesses from the schizophrenia group. In addition, the compounds can also be employed for reducing defects in cognitive ability, i.e. for improving learning ability and memory. The compounds of the general formula I are also suitable for combating the symptoms of Alzheimer's disease. In addition, the substances of the general formula I according to the invention are suitable for the prophylaxis and control of cerebral infarctions (apoplexia cerebri), such as cerebral strokes and cerebral ischaemia. The substances are furthermore suitable for the treatment of illnesses such as pathological anxiety states, overexcitation, hyperactivity and attention disorders in children and youths, severe developmental disorders and disorders of social behaviour with mental retardation, depression, obsessive disorders in the narrower (OCD) and broader sense (OCSD), certain sexual dysfunctions, sleeping disorders and disorders in nutrient uptake, and psychiatric symptoms as part of age dementia and dementia of the Alzheimer's type, i.e. illnesses of the central nervous system in the broadest sense.

The compounds of the formula I are likewise suitable for the treatment of extrapyramidal motor diseases, for the treatment of side effects which occur in the treatment of extrapyramidal motor diseases with conventional anti-Parkinson's medicaments, or for the treatment of extrapyramidal symptoms (EPS) induced by neuroleptics.

Extrapyramidal motor diseases are, for example, idiopathic Parkinson's disease, parkinsonian syndrome, dyskinetic choreatic or dystonic syndromes, tremor, Gilles de la Torette syndrome, ballismus, muscle cramps, restless legs syndrome, Wilson's disease, Lewy bodies dementia, Huntington's and Tourette's syndrome.

The compounds according to the invention are also particularly suitable for the treatment of neurodegenerative diseases, such as, for example, lathyrism, Alzheimer's, Parkinson's and Huntington's.

The compounds of the formula I are particularly suitable for the treatment of side effects which occur in the treatment of idiopathic Parkinson's disease with conventional Parkinson's medicaments. They can therefore also be used as add-on therapy in the treatment of Parkinson's disease. Known Parkinson's medicaments are drugs such as L-dopa (levodopa) and L-dopa combined with benserazide or carbidopa, dopamine agonists, such as bromocriptine, apomorphine, cabergoline, pramipexole, ropinirole, pergolide, dihydro-α-ergocriptine or lisuride, and all medicaments which effect stimulation of the dopamine receptor, inhibitors of catechol O-methyl transferase (COMT), such as entacapone or tolcapone, inhibitors of monoamine oxidase (MAO), such as selegiline, and antagonists of N-methyl D-aspartate (NMDA) receptors, such as amantadine or budipine.

The compounds of the general formula I and tolerated salts and solvates thereof can thus be employed as active ingredients for medicaments, such as anxiolytics, antidepressants, neuroleptics and/or antihypertensives.

A measure of the uptake of a medicament active ingredient in an organism is its bioavailability.

If the medicament active ingredient is administered intravenously to the organism in the form of an injection solution, its absolute bioavailability, i.e. the fraction of the drug which reaches the systemic blood, i.e. the general circulation, in unchanged form is 100%.

In the case of oral administration of a therapeutic active ingredient, the active ingredient is generally in the form of a solid in the formulation and must therefore first be dissolved so that it is able to overcome the entry barriers, for example the gastrointestinal tract, the oral mucous membrane, nasal membranes or the skin, in particular the stratum corneum, or can be absorbed by the body. Pharmacokinetic data, i.e. on the bioavailability, can be obtained analogously to the method of J. Shaffer et al, J. Pharm. Sciences, 1999, 88, 313-318.

A further measure of the absorbability of a therapeutic active ingredient is the logD value, since this value is a measure of the lipophilicity of a molecule.

If the compounds of the general formula I are optically active, the formula I covers both each isolated optical antipode and also the corresponding possibly racemic mixtures in any conceivable composition.

The term solvates of the compounds of the formula I is taken to mean adductions of inert solvent molecules onto the compounds of the formula I which form owing to their mutual attractive force. Solvates are, for example, mono- or dihydrates or addition compounds with alcohols, such as, for example, with methanol or ethanol.

The invention relates to the compounds of the formula I and salts and solvates thereof according to Claim 1 and to a process for the preparation of compounds of the formula I and salts and solvates thereof, characterised in that a) a compound of the formula II

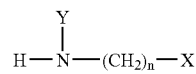

in which

X, Y and n have the meanings indicated in Claim 1, is reacted with a compound of the formula III

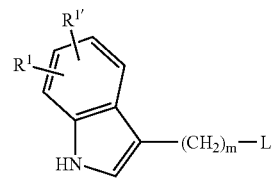

in which

L denotes Cl, Br or I and $R^1$, $R^{1'}$ and m have the meanings indicated in Claim 1, or b) a compound of the formula IV

in which

L denotes Cl, Br or I and X and n have the meanings indicated in Claim 1, is reacted with a compound of the formula V

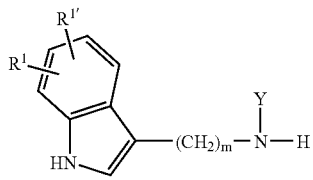

in which $R^1$, $R^{1'}$, Y and m have the meanings indicated in Claim 1, and/or a basic or acidic compound of the formula I is converted into one of its salts or solvates by treatment with an acid or base.

The term pharmaceutically usable derivatives is taken to mean, for example, the salts of the compounds according to the invention and so-called prodrug compounds.

The term prodrug derivatives is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds. A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

A also denotes cycloalkyl.

Cycloalkyl preferably denotes cyclopropyl, cyclobutyl, cyclopentyl, cyclohexyl or cycloheptyl.

A' preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl or benzyl.

—COA or —COA' (acyl) preferably denotes acetyl, propionyl, furthermore also butyryl, pentanoyl, hexanoyl or, for example, benzoyl.

Hal preferably denotes F, Cl or Br, but also I.

OA preferably denotes, for example, methoxy, ethoxy, propoxy, isopropoxy, butoxy or tert-butoxy.

$R^1$ preferably denotes, for example, CN or F, very particularly preferably CN.

$R^{1'}$ preferably denotes H.

m preferably denotes 4.

n preferably denotes 1 or 2.

$R^2$ preferably denotes H, Hal, A, SA, CN, $CONH_2$, COOA', —O—$[C(R^4R^{4'})]_p$Ar, $[C(R^4R^{4'})]_p$Ar or $[C(R^4R^{4'})]_p$Het, where Het preferably denotes chromen-2-onyl, thienyl, pyridinyl, pyrimidinyl, indolyl, furyl, pyrrolyl, isoxazolyl imidazolyl, thiazolyl, triazolyl, tetrazolyl, quinolyl or isoquinolyl, each of which is unsubstituted or monosubstituted by Hal or COOA', and Ar preferably denotes phenyl.

$R^3$ preferably denotes H, A, Hal or CN.

$R^2$ and $R^3$ preferably together also denote —CH=CH—CH=CH—.

$R^4$ and $R^{4'}$ preferably denote H.

Ar denotes, for example, unsubstituted phenyl, naphthyl or biphenyl, furthermore preferably phenyl, naphthyl or biphenyl, each of which is mono-, di- or trisubstituted by, for example, A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

Ar very particularly preferably denotes phenyl.

Het, apart from the possible substituents, denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl, 2,1,3-benzoxadiazol-5-yl or chromenyl. The heterocyclic radicals may also be partially or fully hydrogenated. Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)-phenyl or also 3,4-dihydro-2H-1,5-benzodioxepin-6- or -7-yl, furthermore preferably 2,3-dihydrobenzofuranyl or 2,3-dihydro-2-oxofuranyl.

Het particularly preferably denotes chromen-2-onyl, thienyl, pyridinyl, pyrimidinyl, indolyl, furyl, pyrrolyl, isoxazolyl imidazolyl, thiazolyl, triazolyl, tetrazolyl, quinolyl or isoquinolyl, each of which is unsubstituted or monosubstituted by Hal or COOA'.

Accordingly, the invention relates, in particular, to the compounds of the formula I in which at least one of the said radicals has one of the preferred meanings indicated above. Some preferred groups of compounds can be expressed by the following sub-formulae Ia to Ih, which conform to the formula I and in which the radicals not designated in greater detail have the meaning indicated for the formula I, but in which in Ia $R^1$ denotes CN or F,
  $R^{1'}$ denotes H;
in Ib $R^4$, $R^{4'}$ denote H;
in Ic $R^2$ denotes H, Hal, A, SA, CN, $CONH_2$, COOA', —O—[C($R^4R^{4'}$)]$_p$Ar, [C($R^4R^{4'}$)]$_p$Ar or [C($R^4R^{4'}$)]Het,
  $R^3$ denotes H, A, Hal or CN,
  $R^2$ and $R^3$ together also denote —CH=CH—CH=CH—;
in Id Het denotes chromen-2-onyl, thienyl, pyridinyl, pyrimidinyl, indolyl, furyl, pyrrolyl, isoxazolyl, imidazolyl, thiazolyl, triazolyl, tetrazolyl, quinolyl or isoquinolyl, each of which is unsubstituted or monosubstituted by Hal or COOA';
in Ie Ar denotes phenyl which is unsubstituted or mono-, di- or trisubstituted by Hal;
in If

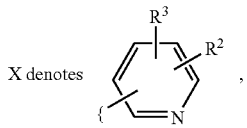

$R^1$ denotes CN or F,
$R^{1'}$ denotes H,
$R^2$ denotes H, Hal, A, SA, CN, $CONH_2$, COOA', —O—[C($R^4R^{4'}$)]$_p$Ar, [C($R^4R^{4'}$)]$_p$Ar or [C($R^4R^{4'}$)]$_p$Het,
$R^3$ denotes H, A, Hal or CN,
$R^2$ and $R^3$ together also denote —CH=CH—CH=CH—,
Het denotes chromen-2-onyl, thienyl, pyridinyl, pyrimidinyl, indolyl, furyl, pyrrolyl, isoxazolyl, imidazolyl, thiazolyl, triazolyl, tetrazolyl, quinolyl or isoquinolyl, each of which is unsubstituted or monosubstituted by Hal or COOA',
Ar denotes phenyl which is unsubstituted or mono-, di- or trisubstituted by Hal,
p denotes 0 or 1;
in Ig

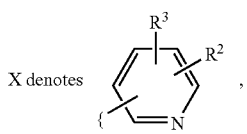

$R^1$ denotes CN or F,
$R^{1'}$ denotes H,
$R^2$ denotes H, Hal, A, SA, CN, $CONH_2$, COOA', —O—[C($R^4R^{4'}$)]$_p$Ar, [C($R^4R^{4'}$)]$_p$Ar or [C($R^4R^{4'}$)]$_p$Het,
$R^3$ denotes H, A, Hal or CN, $R^2$ and $R^3$ together also denote —CH=CH—CH=CH—,
Ar denotes phenyl,
p denotes 0 or 1;
in Ih

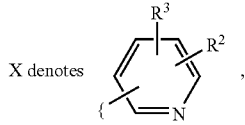

$R^1$ denotes CN or F,
$R^{1'}$ denotes H,
$R^2$ denotes H, Hal, A, SA, CN, $CONH_2$, COOA', —O—[C($R^4R^{4'}$)]$_p$Ar, [C($R^4R^{4'}$)]$_p$Ar,
$R^3$ denotes H, A, Hal or CN,
$R^2$ and $R^3$ together also denote —CH=CH—CH=CH—,
$R^4$, $R^{4'}$ denote H,
Ar denotes phenyl,
p denotes 0 or 1;

and pharmaceutically usable derivatives, solvates and stereoisomers thereof, including mixtures thereof in all ratios.

The compounds of the formula I according to Claim 1 and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I according to claim 1.

The starting compounds of the formula II and III are generally known. If they are novel, however, they can be prepared by methods known per se.

Compounds of the formula I can be prepared by nucleophilic substitution of the leaving group L of the compounds of the formula III, where L denotes Cl, Br or I, by the amine nitrogen of the compound of the formula II under standard conditions.

The reaction conditions for nucleophilic substitutions, as described above, are adequately known to the person skilled in the art, see also Organikum [Practical Organic Chemistry], 17th Edition, Deutscher Verlag für Wissenschaften, Berlin 1988.

The reaction is generally carried out in an inert solvent, in the presence of an acid-binding agent, preferably an alkali or alkaline earth metal hydroxide, carbonate or bicarbonate, or another salt of a weak acid of the alkali or alkaline earth metals, preferably of potassium, sodium, calcium or caesium. The addition of an organic base, such as ethyldiisopropylamine, triethylamine, dimethylaniline, pyridine or quinoline, or an excess of the component of the formula II or of the alkylation derivative of the formula III may also be favourable. The reaction time, depending on the conditions used, is between a few minutes and 14 days, the reaction temperature is between about 0° and 150°, normally between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or mono, ethyl ether, ethylene glycol dimethyl ether (diglyme); ketones, such as acetone or butanone; amides, such as acetamide, N-methylpyrrolidone, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Compounds of the formula I can furthermore be obtained by reacting compounds of the formula IV with compounds of the formula V.

The starting compounds of the formula IV and V are generally known. If they are novel, however, they can be prepared by methods known per se.

The reaction conditions are analogous to those of the reaction between compounds of the formula II and compounds of the formula III.

Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide or reacted with $CH_3$—$C(=NH)$—$OEt$, advantageously in an inert solvent, such as dichloromethane or THF, and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, para-chlorophenoxyisobutyric acid, cyclohexanecarboxylic acid, glucose 1-phosphate, naphthalenemono- and -disulfonic acids or laurylsulfuric acid. Salts with physiologically unacceptable acids, for example picrates, can be used to isolate and/or purify the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

The invention also relates to the compounds of the formula I according to Claim 1 and physiologically acceptable salts or solvates thereof as medicament active ingredients.

The invention furthermore relates to compounds of the formula I and physiologically acceptable salts or solvates thereof as $5HT_{1A}$ and/or $5HT_{1D}$ agonists and as inhibitors of 5-HT reuptake.

The invention also relates to the compounds of the formula I according to Claim 1 and physiologically acceptable salts or solvates thereof for use in combating diseases.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of a medicament (pharmaceutical composition), in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

The invention furthermore relates to the use of a compound of the general formula I and/or pharmaceutically usable derivatives, solvates and stereoisomers thereof, including mixtures thereof in all ratios, for the preparation of a medicament which is suitable for the treatment of human or animal illnesses, in particular illnesses of the central nervous system, such as pathological stress states, depression and/or psychoses, for reducing side effects in the treatment of high blood pressure (for example with a-methyldopa), for the treatment of endoclinological and/or gynaecological illnesses, for example for the treatment of agromegaly, hypogonadism, secondary amenorrhoea, post-menstrual syndrome and undesired lactation in puberty and for the prophylaxis and therapy of cerebral illnesses (for example migraine), in particular in geriatrics, in a similar manner as certain ergot alkaloids, and for the control and prophylaxis of cerebral infarction (apoplexia cerebri), such as cerebral strokes and cerebral ischaemia, for the treatment of extrapyramidal motor diseases, for the treatment of side effects which occur in the treatment of extrapyramidal motor diseases with conventional anti-Parkinson's medicaments, or for the treatment of extrapyramidal symptoms (EPS) induced by neuroleptics. In addition, the pharmaceutical compositions and medicaments which comprise a compound of the general formula I are suitable for improving cognitive ability and for the treatment of the symptoms of Alzheimer's disease. In particular, medicaments of this type are suitable for the treatment of mental illnesses from the schizophrenia group and for combating psychotic anxiety states. For the purposes of the invention, the term treatment includes the prophylaxis and therapy of human or animal illnesses.

The invention furthermore relates to the use of compounds of the formula I and/or pharmaceutically usable derivatives, solvates and stereoisomers thereof, including mixtures thereof in all ratios, for the preparation of a medicament for combating diseases which are associated with the serotonin neurotransmitter system and in which high-affinity serotonin receptors (5-HT$_{1A}$ receptors) and/or 5-HT$_{1D}$ receptors are involved.

The invention furthermore relates to the use of compounds of the formula I and/or pharmaceutically usable derivatives, solvates and stereoisomers thereof, including mixtures thereof in all ratios, for the preparation of a medicament as anxiolytic, antidepressant, neuroleptic and/or antihypertensive.

The substances of the general formula I are normally administered analogously to known, commercially available pharmaceutical compositions (for example bromocriptine and dihydroergocornine), preferably in doses of between 0.2 and 500 mg, in particular between 0.2 and 15 mg, per dosage unit. The daily dosage unit is between 0.001 and 10 mg per kg of body weight. Low doses (of between 0.2 and 1 mg per dosage unit, from 0.001 to 0.005 mg per kg of body weight) are particularly suitable for pharmaceutical compositions for the treatment of migraine. A dose of between 10 and 50 mg per dosage unit is preferred for other indications. However, the dose to be administered depends on a multiplicity of factors, for example on the efficacy of the corresponding component, the age, the body weight and the general state of health of the patient.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may comprise, for example, separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel, by preparative HPLC and/or by crystallisation. The purified compounds are optionally freeze-dried.

Mass spectrometry (MS):
   EI (electron impact ionisation) M$^+$
   FAB (fast atom bombardment) (M+H)$^+$
   ESI (electrospray ionisation) (M+H)$^+$ (unless stated otherwise)

EXAMPLE 1

The synthesis of the indole unit is carried out analogously to the following scheme:

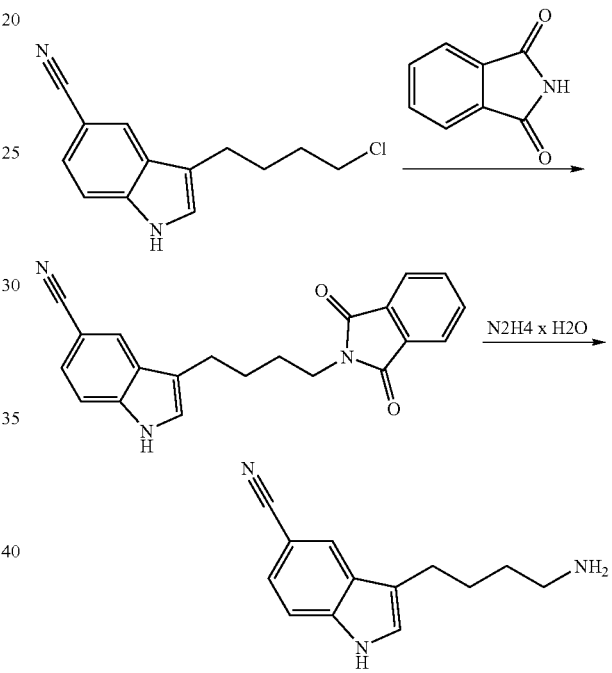

The synthesis of 3-{4-[(5-bromopyridin-3-ylmethyl)amino]butyl}-1H-indole-5-carbonitrile is carried out analogously to the following scheme:

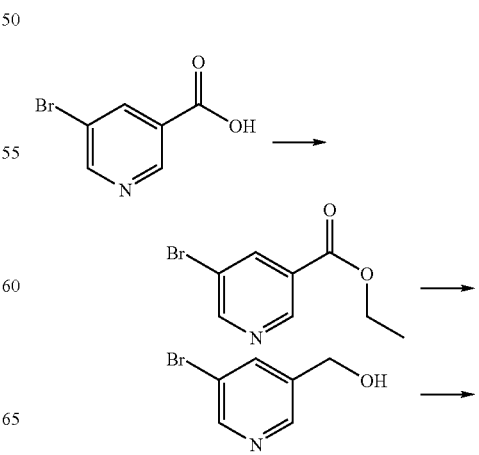

-continued

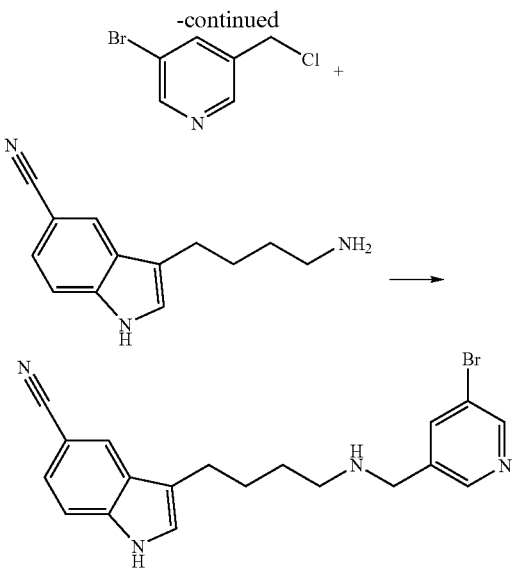

1.1 1.3 g of ethyl 5-bromonicotinate are initially introduced in 40 ml of tert-butanol, and 427 mg of sodium borohydride are added. The entire mixture is heated under reflux (100° C.) and under $N_2$ for one hour. 6 ml of methanol are then added. The mixture is stirred overnight. 10 ml of water is added to the reaction solution. The mixture is then extracted with dichloromethane, dried using sodium sulfate and evaporated in a rotary evaporator, giving 300 mg of (5-bromopyridin-3-yl)methanol.

1.2 300 mg of the crude product (5-bromopyridin-3-yl) methanol obtained previously are dissolved in 20 of toluene. 0.2 ml of thionyl chloride are added, and the mixture is stirred at 100° C. for one hour. The mixture is then evaporated in a rotary evaporator. The oily residue comprises 3-bromo-5-chloromethylpyridine (315 mg).

1.3 300 mg of 3-bromo-5-chloromethylpyridine and 331 mg of 3-(4-aminobutyl)-1H-indole-5-carbonitrile are combined in acetonitrile. 415 mg of potassium carbonate and a spatula tip of potassium iodide are then added. The mixture is boiled under reflux overnight. The mixture is evaporated in a rotary evaporator, and water is added. The mixture is extracted twice with ethyl acetate, dried using sodium sulfate, filtered and evaporated in a rotary evaporator.

390 mg of the crude product are purified with the aid of preparative HPLC:
HPLC column: RP 18 (15 mm) Lichrosorb
Eluent: A 98 of $H_2O$, 2 of $CH_3CN$, 0.1% of TFA B 10 of $H_2O$, 90 of $CH_3CN$, 0.1% of TFA
UV detection: 225 NM; 1 range
Flow rate: 10 ml
Fraction 19-23 contains the desired compound 3-{4-[(5-bromopyridin-3-yl-methyl)amino]butyl}-1H-indole-5-carbonitrile, bis-TFA salt.
Yield: 143 mg
HPLC-ESI-MS $(M+H)^+$ 383.

EXAMPLE 2

Preparation of 3-{4-[(2-chloro-6-methylpyridin-4-ylmethyl)amino]butyl}-1H-indole-5-carbonitrile 2.1 1.94 g of ethyl 2-chloro-6-methylisonicotinate are initially introduced in 36 ml of tert-butanol, 0.93 g of sodium borohydride is added, and the mixture is heated to reflux under nitrogen (bath temperature about 120 C). After 1 h, 9 ml of methanol are added slowly, boiled under reflux overnight.

Conventional work-up gives 1.15 g of (2-chloro-6-methylpyridin-4-yl)-methanol.

2.2 1.14 g of (2-chloro-6-methylpyridin-4-yl)methanol are initially introduced in 50 ml of toluene, and 1.05 ml of thionyl chloride are slowly added dropwise with ice cooling. The mixture is boiled under reflux overnight. After cooling, the solvent is removed, giving 2-chloro-4-chloromethyl-6-methylpyridine as brown oil (1.1 g).

2.3 213 mg of 2-chloro-4-chloromethyl-6-methylpyridine and 250 mg of 3-(4-aminobutyl)-1H-indole-5-carbonitrile are combined in acetonitrile. 276 mg of potassium carbonate and about 3 mg of potassium iodide are added thereto. The mixture is boiled under reflux overnight. The mixture is cooled, and the solvent is then removed. 20 ml of water and 20 ml of ethyl acetate are then added.

Conventional work-up gives a brown residue (0.4 g).
Purification is carried out by flash chromatography (eluent: $CH_2Cl_2$/MeOH 97:3), giving 150 mg of 3-{4-[(2-chloro-6-methylpyridin-4-ylmethyl)amino]-butyl}-1H-indole-5-carbonitrile, HPLC-ESI-MS $(M+H)^+$ 353.

EXAMPLE 3

Preparation of 3-{4-[(quinolin-3-ylmethyl)amino]butyl}-1H-indole-5-carbonitrile 126 mg of quinoline-3-carboxaldehyde and 200 mg of 3-(4-aminobutyl)-1H-indole-5-carbonitrile are combined in a mixture of 5 ml of 1,2-dichloroethane and 2.5 ml of THF. 55 mg of glacial acetic acid are added, and the mixture is stirred at room temperature for 3 hours. 380 mg of $NaB(OAc)_3$ are then added, and stirring is continued at RT for 2 days.

Saturated $NaHCO_3$ solution is added to the batch, which is extracted twice with ethyl acetate, dried over $Na_2SO_4$, filtered and evaporated in a rotary evaporator. Chromatography in the Flash-Master with EE/MeOH as eluent give 73 mg of the desired product, HPLC-MS $(M+H)^+$ 355.

The following compounds are obtained analogously
3-{4-[(quinolin-2-ylmethyl)amino]butyl}-1H-indole-5-carbonitrile, HPLC-MS $(M+H)^+$ 355;
3-{4-[(quinolin-4-ylmethyl)amino]butyl}-1H-indole-5-carbonitrile, HPLC-MS $(M+H)^+$ 355.

EXAMPLE 4

The following compounds are obtained analogously to Example 1
3-{4-[(pyridin-3-ylmethyl)amino]butyl}-1H-indole-5-carbonitrile, dihydrochloride, HPLC-MS $(M+H)^+$ 305;
3-{4-[(pyridin-2-ylmethyl)amino]butyl}-1H-indole-5-carbonitrile, dihydrochloride, HPLC-MS $(M+H)^+$ 305;
3-{4-[(pyridin-4-ylmethyl)amino]butyl}-1H-indole-5-carbonitrile, dihydrochloride, HPLC-MS $(M+H)^+$ 305;
3-(4-{[5-(4-fluorophenyl)pyridin-3-ylmethyl]amino}butyl)-1H-indole-5-carbonitrile, HPLC-MS $(M+H)^+$ 399;
3-[4-(2-pyridin-4-ylethylamino]butyl]-1H-indole-5-carbonitrile, HPLC-MS $(M+H)^+$ 319;
3-{4-[(2,6-dichloropyridin-4-ylmethyl)amino]butyl}-1H-indole-5-carbonitrile, HPLC-MS $(M+H)^+$ 373;
3-{4-[(2-chloropyridin-4-ylmethyl)amino]butyl}-1H-indole-5-carbonitrile, HPLC-MS $(M+H)^+$ 339;
3-{4-[(2-methylpyridin-3-ylmethyl)amino]butyl}-1H-indole-5-carbonitrile, HPLC-MS $(M+H)^+$ 318;

3-{4-[(6-chloropyridin-3-ylmethyl)amino]butyl}-1H-indole-5-carbonitrile, bis-TFA salt, HPLC-MS (M+H)$^+$ 339;

3-(4-{[2-(4-chlorophenoxy)pyridin-3-ylmethyl]amino}butyl)-1H-indole-5-carbonitrile, TFA salt, HPLC-MS (M+H)$^+$ 431;

3-{4-[(2-methylsulfanylpyridin-3-ylmethyl)amino]butyl}-1H-indole-5-carbonitrile, TFA salt, HPLC-MS (M+H)$^+$ 351;

3-{4-[(2,5-dichloropyridin-3-ylmethyl)amino]butyl}-1H-indole-5-carbonitrile, bis-TFA salt, HPLC-MS (M+H)$^+$ 374;

3-{4-[(2,6-dichloropyridin-3-ylmethyl)amino]butyl}-1H-indole-5-carbonitrile, bis-TFA salt, HPLC-MS (M+H)$^+$ 374;

3-{4-[(5-methylpyridin-3-ylmethyl)amino]butyl}-1H-indole-5-carbonitrile, bis-TFA salt, HPLC-MS (M+H)$^+$ 318;

3-{4-[(6-trifluoromethylpyridin-3-ylmethyl)amino]butyl}-1H-indole-5-carbonitrile, HPLC-MS (M+H)$^+$ 373;

3-{4-[(4-phenylpyridin-2-ylmethyl)amino]butyl}-1H-indole-5-carbonitrile, HPLC-MS (M+H)$^+$ 381;

3-{4-[(4-phenylpyridin-3-ylmethyl)amino]butyl}-1H-indole-5-carbonitrile, HPLC-MS (M+H)$^+$ 381;

3-{4-[(5-cyano-6-methylsulfanylpyridin-2-ylmethyl)amino]butyl}-1H-indole-5-carbonitrile, HPLC-MS (M+H)$^+$ 376;

3-{4-[(5-phenylpyridin-3-ylmethyl)amino]butyl}-1H-indole-5-carbonitrile, HPLC-MS (M+H)$^+$ 381;

3-{4-[(5-phenylpyridin-2-ylmethyl)amino]butyl}-1H-indole-5-carbonitrile, HPLC-MS (M+H)$^+$ 381;

3-[4-(methylpyridin-3-ylmethylamino)butyl]-1H-indole-5-carbonitrile, HPLC-MS (M+H)$^+$ 319.

The examples below relate to pharmaceutical compositions:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

The invention claimed is:

1. A compound of formula I

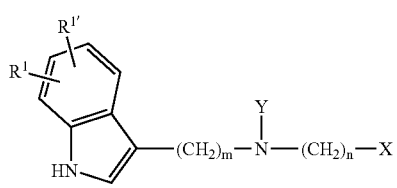

in which

X is

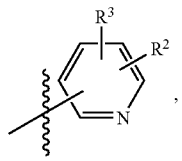

Y is H or A',
R[1] is CN or F,
R[1'] is H,
R[2] is H, Hal, A, SA, CN, CONH$_2$, COOA', —O—[C(R[4]R[4'])]$_p$Ar, [C(R[4]R[4'])]$_p$Ar or [C(R[4]R[4'])]$_p$Het,
R[3] is H, A, Hal or CN, or
R[2] and R[3] together are —CH=CH—CH=CH—,
R[4] and R[4'] are each H,
Ar is phenyl which is unsubstituted or mono-, di- or trisubstituted by Hal,
Het is chromen-2-onyl, thienyl, pyridinyl, pyrimidinyl, indolyl, furyl, pyrrolyl, isoxazolyl, imidazolyl, thiazolyl, triazolyl, tetrazolyl, quinolyl or isoquinolyl, each of which is unsubstituted or monosubstituted by Hal or COOA',
A is unbranched or branched alkyl having 1-10 C atoms, in which one or two CH$_2$ groups are optionally, each independently, replaced by a —CH=CH— group and/or 1-7 H atoms are optionally replaced by F and/or Cl,
A' is alkyl having 1 to 6 C atoms or benzyl,
Hal is F, Cl, Br or I,
m is 2, 3, 4, 5 or 6,
n is 1, 2, 3 or 4, and
p is 0, 1, 2, 3, 4, 5 or 6,
or a pharmaceutically acceptable salt, or stereoisomer thereof, or a mixture thereof.

2. A compound according to claim 1, in which
p is 0 or 1.

3. A compound according to claim 1, in which
Ar is phenyl, and
p is 0 or 1.

4. A compound according to claim 1, in which
Ar is phenyl, and
p is 0 or 1.

5. A compound according to claim 1, which is
3-{4-[(5-bromopyridin-3-ylmethyl)amino]butyl}-1H-indole-5-carbonitrile,
3-{4-[(pyridin-3-ylmethyl)amino]butyl}-1H-indole-5-carbonitrile,
3-{4-[(pyridin-2-ylmethyl)amino]butyl}-1H-indole-5-carbonitrile,
3-{4-[(pyridin-4-ylmethyl)amino]butyl}-1H-indole-5-carbonitrile,
3-(4-{[5-(4-fluorophenyl)pyridin-3-ylmethyl]amino}butyl)-1H-indole-5-carbonitrile,
3-{4-[(quinolin-3-ylmethyl)amino]butyl}-1H-indole-5-carbonitrile,
3-[4-(2-pyridin-4-ylethylamino)butyl]-1H-indole-5-carbonitrile,
3-{4-[(2,6-dichloropyridin-4-ylmethyl)amino]butyl}-1H-indole-5-carbonitrile,
3-{4-[(2-chloro-6-methylpyridin-4-ylmethyl)amino]butyl}-1H-indole-5-carbonitrile,
3-{4-[(2-chloropyridin-4-ylmethyl)amino]butyl}-1H-indole-5-carbonitrile,
3-{4-[(2-methylpyridin-3-ylmethyl)amino]butyl}-1H-indole-5-carbonitrile,
3-{4-[(6-chloropyridin-3-ylmethyl)amino]butyl}-1H-indole-5-carbonitrile,
3-(4-{[2-(4-chlorophenoxy)pyridin-3-ylmethyl]amino}butyl)-1H-indole-5-carbonitrile,
3-{4-[(2-methylsulfanylpyridin-3-ylmethyl)amino]butyl}-1H-indole-5-carbonitrile,
3-{4-[(2,5-dichloropyridin-3-ylmethyl)amino]butyl}-1H-indole-5-carbonitrile,
3-{4-[(2,6-dichloropyridin-3-ylmethyl)amino]butyl}-1H-indole-5-carbonitrile,
3-{4-[(5-methylpyridin-3-ylmethyl)amino]butyl}-1H-indole-5-carbonitrile,
3-{4-[(6-trifluoromethylpyridin-3-ylmethyl)amino]butyl}-1H-indole-5-carbonitrile,
3-{4-[(quinolin-2-ylmethyl)amino]butyl}-1H-indole-5-carbonitrile,
3-{4-[(4-phenylpyridin-2-ylmethyl)amino]butyl}-1H-indole-5-carbonitrile,
3-{4-[(quinolin-4-ylmethyl)amino]butyl}-1H-indole-5-carbonitrile,
3-{4-[(4-phenylpyridin-3-ylmethyl)amino]butyl}-1H-indole-5-carbonitrile,
3-{4-[(5-cyano-6-methylsulfanylpyridin-2-ylmethyl)amino]butyl}-1H-indole-5-carbonitrile,
3-{4-[(5-phenylpyridin-3-ylmethyl)amino]butyl}-1H-indole-5-carbonitrile,
3-{4-[(5-phenylpyridin-2-ylmethyl)amino]butyl}-1H-indole-5-carbonitrile, or
3-[4-(methylpyridin-3-ylmethylamino)butyl]-1H-indole-5-carbonitrile.

6. A process for preparing a compound of formula I according to claim 1, comprising
a) reacting a compound of formula II

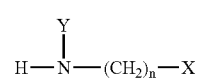

II in which
X is

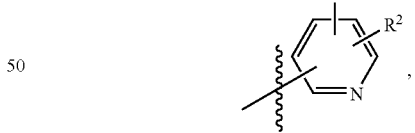

Y is H or A',
R[2] is H, Hal, A, SA, CN, CONH$_2$, COOA', —O—[C(R[4]R[4'])]$_p$Ar, [C(R[4]R[4'])]$_p$Ar or [C(R[4]R[4'])]$_p$Het,
R[3] is H, A, Hal or CN, or
R[2] and R[3] together are —CH=CH—CH=CH—,
R[4] and R[4'] are each H,
Ar is phenyl which is unsubstituted or mono-, di- or trisubstituted by Hal,
Het is chromen-2-onyl, thienyl, pyridinyl, pyrimidinyl, indolyl, furyl, pyrrolyl, isoxazolyl, imidazolyl, thiazolyl, triazolyl, tetrazolyl, quinolyl or isoquinolyl, each of which is unsubstituted or monosubstituted by Hal or COOA', A is unbranched or branched alkyl having 1-10 C atoms, in which one or two $CH_2$ groups are optionally, each independently, replaced by a —CH=CH— group and/or 1-7 H atoms are optionally replaced by F and/or Cl, A' is alkyl having 1 to 6 C atoms or benzyl, Hal is F, Cl, Br or I, n is 1, 2, 3 or 4, and p is 0, 1, 2, 3, 4, 5 or 6, with a compound of formula III

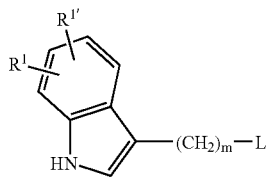

in which

L is Cl, Br or I, $R^1$ is CN or F, $R^{1'}$ is H, and m is 2, 3, 4, 5 or 6, or b) reacting a compound of formula IV

in which

L is Cl, Br or I,

X is

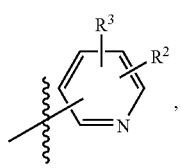

$R^2$ is H, Hal, A, SA, CN, $CONH_2$, COOA', —O—[C$(R^4R^{4'})]_p$Ar, [C$(R^4R^{4'})]_p$Ar or [C$(R^4R^{4'})]_p$Het, $R^3$ is H, A, Hal or CN, or $R^2$ and $R^3$ together are —CH=CH—CH=CH—, $R^4$ and $R^{4'}$ are each H, Ar is phenyl which is unsubstituted or mono-, di- or trisubstituted by Hal, Het is chromen-2-onyl, thienyl, pyridinyl, pyrimidinyl, indolyl, furyl, pyrrolyl, isoxazolyl, imidazolyl, thiazolyl, triazolyl, tetrazolyl, quinolyl or isoquinolyl, each of which is unsubstituted or monosubstituted by Hal or COOA', A is unbranched or branched alkyl having 1-10 C atoms, in which one or two $CH_2$ groups are optionally, each independently, replaced by a —OH=CH— group and/or 1-7 H atoms are optionally replaced by F and/or Cl, A' is alkyl having 1 to 6 C atoms or benzyl, Hal is F, Cl, Br or I, n is 1, 2, 3 or 4, and p is 0, 1, 2, 3, 4, 5 or 6, with a compound of formula V

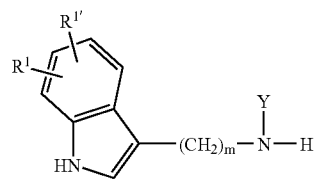

in which

Y is H or A', $R^1$ is CN or F, $R^{1'}$ is H,

A' is alkyl having 1 to 6 C atoms or benzyl, and m is 2, 3, 4, 5 or 6, and/or converting a basic or acidic compound of formula I into one of its salts and/or solvate by treatment with an acid or base, or with a solvent.

7. A pharmaceutical composition comprising a compound according to claim 1 and a pharmaceutically acceptable excipient and/or adjuvant.

8. A method for treating anxiety, depression, or psychoses, comprising administering to a subject in need thereof an effective amount of a compound of claim 1.

9. A kit comprising separate packs of a compound according to claim 1, and a pharmaceutically acceptable excipient and/or adjuvant.

10. A compound of formula I

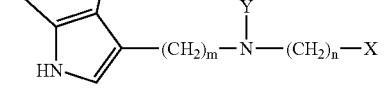

in which

X is

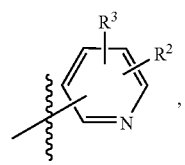

Y is H or A', $R^1$ is CN or F, $R^{1'}$ is H, $R^2$ is H, Hal, A, SA, CN, $CONH_2$, COOA', —O—[C$(R^4R^{4'})]_p$Ar, [C$(R^4R^{4'})]_p$Ar or [C$(R^4R^{4'})]_p$Het, $R^3$ is H, A, Hal or CN, or $R^2$ and $R^3$ together are —CH=CH—CH=CH—, $R^4$ and $R^{4'}$ are each H, Ar is phenyl which is unsubstituted or mono-, di- or trisubstituted by Hal, Het is chromen-2-onyl, thienyl, pyridinyl, pyrimidinyl, indolyl, furyl, pyrrolyl, isoxazolyl, imidazolyl, thiazolyl, triazolyl, tetrazolyl, quinolyl or isoquinolyl, each of which is unsubstituted or monosubstituted by Hal or COOA', A is unbranched or branched alkyl having 1-10 C atoms, in which one or two $CH_2$ groups are optionally, each independently, replaced by a —CH=CH— group and/or 1-7 H atoms are optionally replaced by F and/or Cl, A' is alkyl having 1 to 6 C atoms or benzyl, Hal is F, Cl, Br or I, m is 2, 3, 4, 5 or 6, n is 1, 2, 3 or 4, and p is 0, 1, 2, 3, 4, 5 or 6, or a pharmaceutically acceptable salt thereof.

11. A pharmaceutically acceptable salt of a compound of claim 10, wherein the compound is
- 3-{4-[(5-bromopyridin-3-ylmethyl)amino]butyl}-1H-indole-5-carbonitrile,
- 3-{4-[(pyridin-3-ylmethyl)amino]butyl}-1H-indole-5-carbonitrile,
- 3-{4-[(pyridin-2-ylmethyl)amino]butyl}-1H-indole-5-carbonitrile,
- 3-{4-[(pyridin-4-ylmethyl)amino]butyl}-1H-indole-5-carbonitrile,
- 3-(4-{[5-(4-fluorophenyl)pyridin-3-ylmethyl]amino}butyl)-1H-indole-5-carbonitrile,
- 3-{4-[(quinolin-3-ylmethyl)amino]butyl}-1H-indole-5-carbonitrile,
- 3-[4-(2-pyridin-4-ylethylamino)butyl]-1H-indole-5-carbonitrile,
- 3-{4-[(2,6-dichloropyridin-4-ylmethyl)amino]butyl}-1H-indole-5-carbonitrile,
- 3-{4-[(2-chloro-6-methylpyridin-4-ylmethyl)amino]butyl}-1H-indole-5-carbonitrile,
- 3-{4-[(2-chloropyridin-4-ylmethyl)amino]butyl}-1H-indole-5-carbonitrile,
- 3-{4-[(2-methylpyridin-3-ylmethyl)amino]butyl}-1H-indole-5-carbonitrile,
- 3-{4-[(6-chloropyridin-3-ylmethyl)amino]butyl}-1H-indole-5-carbonitrile,
- 3-(4-{[2-(4-chlorophenoxy)pyridin-3-ylmethyl]amino}butyl)-1H-indole-5-carbonitrile,
- 3-{4-[(2-methylsulfanylpyridin-3-ylmethyl)amino]butyl}-1H-indole-5-carbonitrile,
- 3-{4-[(2,5-dichloropyridin-3-ylmethyl)amino]butyl}-1H-indole-5-carbonitrile,
- 3-{4-[(2,6-dichloropyridin-3-ylmethyl)amino]butyl}-1H-indole-5-carbonitrile,
- 3-{4-[(5-methylpyridin-3-ylmethyl)amino]butyl}-1H-indole-5-carbonitrile,
- 3-{4-[(6-trifluoromethylpyridin-3-ylmethyl)amino]butyl}-1H-indole-5-carbonitrile,
- 3-{4-[(quinolin-2-ylmethyl)amino]butyl}-1H-indole-5-carbonitrile,
- 3-{4-[(4-phenylpyridin-2-ylmethyl)amino]butyl}-1H-indole-5-carbonitrile,
- 3-{4-[(quinolin-4-ylmethyl)amino]butyl}-1H-indole-5-carbonitrile,
- 3-{4-[(4-phenylpyridin-3-ylmethyl)amino]butyl}-1H-indole-5-carbonitrile,
- 3-{4-[(5-cyano-6-methylsulfanylpyridin-2-ylmethyl)amino]butyl}-1H-indole-5-carbonitrile,
- 3-{4-[(5-phenylpyridin-3-ylmethyl)amino]butyl}-1H-indole-5-carbonitrile,
- 3-{4-[(5-phenylpyridin-2-ylmethyl)amino]butyl}-1H-indole-5-carbonitrile, or
- 3-[4-(methylpyridin-3-ylmethylamino)butyl]-1H-indole-5-carbonitrile.

* * * * *

UNITED STATES PATENT AND TRADEMARK OFFICE
CERTIFICATE OF CORRECTION

PATENT NO. : 7,432,282 B2  Page 1 of 1
APPLICATION NO. : 10/535916
DATED : October 7, 2008
INVENTOR(S) : Gunter Holzemann It is certified that error appears in the above-identified patent and that said Letters Patent is hereby corrected as shown below:

Column 17, line 14, reads "$R^1$'" should read -- $R^{1'}$ --
Column 17, line 16, reads "$R^4$'" should read -- $R^{4'}$ --
Column 17, line 16, reads "$R^4$'" should read -- $R^{4'}$ --
Column 17, line 16, reads "$R^4$'" should read -- $R^{4'}$ --
Column 17, line 19, reads "$R^4$'" should read -- $R^{4'}$ --
Column 17, line 42 – 43, claim 3, reads "Ar is phenyl, and p is 0 or 1." should read -- Ar is phenyl. --
Column 18, line 57, reads "$R^4$'" should read -- $R^{4'}$ --
Column 18, line 57, reads "$R^4$'" should read -- $R^{4'}$ --
Column 18, line 57, reads "$R^4$'" should read -- $R^{4'}$ --
Column 18, line 60, reads "$R^4$'" should read -- $R^{4'}$ --
Column 19, line 25, reads "$R^1$'" should read -- $R^{1'}$ --
Column 19, line 48, reads "$R^4$'" should read -- $R^{4'}$ --
Column 19, line 48, reads "$R^4$'" should read -- $R^{4'}$ --
Column 19, line 48, reads "$R^4$'" should read -- $R^{4'}$ --
Column 19, line 51, reads "$R^4$'" should read -- $R^{4'}$ --
Column 19, line 61, reads "—OH=CH—" should read -- —CH=CH— --
Column 20, line 16, reads "$R^1$'" should read -- $R^{1'}$ --
Column 20, line 57, reads "$R^1$'" should read -- $R^{1'}$ --
Column 20, line 59, reads "$R^4$'" should read -- $R^{4'}$ --
Column 20, line 59, reads "$R^4$'" should read -- $R^{4'}$ --
Column 20, line 59, reads "$R^4$'" should read -- $R^{4'}$ --
Column 20, line 63, reads "$R^4$'" should read -- $R^{4'}$ --

Signed and Sealed this

Twenty-fourth Day of March, 2009

JOHN DOLL
*Acting Director of the United States Patent and Trademark Office*